(12) United States Patent
Bruzzi et al.

(10) Patent No.: US 8,563,936 B2
(45) Date of Patent: Oct. 22, 2013

(54) BIDIMENSIONAL DOSIMETRIC DETECTOR

(75) Inventors: Mara Bruzzi, Florence (IT); Marta Bucciolini, Florence (IT); Cinzia Talamonti, Florence (IT); David Menichelli, Vernio (IT)

(73) Assignee: Universita' Degli Studi Firenze, Firenze (IT)

( * ) Notice: Subject to any disclaimer, the term of this patent is extended or adjusted under 35 U.S.C. 154(b) by 982 days.

(21) Appl. No.: 12/308,993

(22) PCT Filed: Jun. 22, 2007

(86) PCT No.: PCT/IB2007/001850
§ 371 (c)(1),
(2), (4) Date: Nov. 20, 2009

(87) PCT Pub. No.: WO2008/004091
PCT Pub. Date: Jan. 10, 2008

(65) Prior Publication Data
US 2010/0176302 A1    Jul. 15, 2010

(30) Foreign Application Priority Data
Jun. 30, 2006  (IT) ............................. FI2006A000166

(51) Int. Cl.
*G01T 1/20*  (2006.01)
*G01T 1/02*  (2006.01)

(52) U.S. Cl.
USPC ................................. 250/370.07; 250/361 R

(58) Field of Classification Search
USPC .......................................... 250/370.07, 361 R
See application file for complete search history.

(56) References Cited

U.S. PATENT DOCUMENTS

| | | | |
|---|---|---|---|
| 7,582,875 B2 * | 9/2009 | Caccia et al. ............ | 250/370.07 |
| 2005/0082630 A1 * | 4/2005 | Yamanaka .................... | 257/461 |
| 2006/0006488 A1 * | 1/2006 | Kanbe .......................... | 257/443 |
| 2006/0131480 A1 * | 6/2006 | Charbon et al. ........... | 250/214.1 |
| 2007/0075344 A1 | 4/2007 | Yamanaka | |
| 2007/0158740 A1 * | 7/2007 | Yoshikawa et al. .......... | 257/330 |

FOREIGN PATENT DOCUMENTS

EP    1 677 353 A1    7/2006
JP    2001 352 094 A    12/2001

OTHER PUBLICATIONS

Int'l Search Report, Nov. 2, 2007.

* cited by examiner

*Primary Examiner* — Constantine Hannaher
*Assistant Examiner* — Mindy Vu
(74) *Attorney, Agent, or Firm* — Abelman, Frayne & Schwab

(57) ABSTRACT

Bidimensional dosimetric detector, comprising: a monolithic base-matrix (1) made of homoepitaxial silicon with a surface for exposition to the radiation, a plurality of radiation-sensible junction diodes (2) for producing a plurality of electrical signals in response to the radiation, electrical terminals (3) connected to said diodes for feeding said produced electrical signals to an acquisition and processing unit (5), wherein the perimeter of one or more said diodes is defined by a boundary region of the electrical field of same diode.

15 Claims, 3 Drawing Sheets

US 8,563,936 B2

BIDIMENSIONAL DOSIMETRIC DETECTOR

This application claims priority under 35 U.S.C. §119, 120 and/or 365 from Italian Application No. 12/308,993 filed Dec. 20, 2008.

TECHNICAL FIELD

The object of the present invention is a bidimensional dosimetric detector for radiotherapeutic applications.

BACKGROUND ART

Dose detectors for radiotherapy are normally used for a pre-treatment verification of the radiation dose distribution planned for certain treatment procedures. Dosimetric detectors are known to comprise matrixes of radiation-sensible elements by which it is possible to draw instantly a response in digital form to be compared with the expectations of the system for the planning of radiotherapeutic treatment.

The above said dosimetric detectors exhibit some drawbacks.

A first drawback is given by the poor spatial resolution due to the dimension of the sensible elements and to the granularity.

Generally, the main cause of the poor spatial resolutions is the predetermined value of the minimum pitch (centre-to-centre distance) between the sensible elements, which is in the order of 7 mm.

A second drawback is given by the fact that, the sensible elements used in radiotherapy, in general, are produced from standard crystalline silicon (e.g. Czochralski) and, for this reason, they are damaged by lattice defects induced by the passage of the same radiation.

The macroscopic damage due to the rise of lattice-disorder is revealed both by a reduced sensibility, caused by the trapping of minority charge-carriers generated by radiation in the lattice defects, and by an increment of the leakage current due to the production of defects which act as generation-recombination centres.

Under these conditions, the sensibility of the device is directly proportional to the diffusion length of the minority carriers L.

Generally, L is in the order of 100-400 µm, while the total thickness S of the device is in the order of 300-500 µm; under these operating conditions, the active thickness W is L and not S.

Having demonstrated that the sensibility is a function of the absorbed dose, with a very strong dependence up to 5 kGy and that, after this value, the reduction becomes less important and its trend linear, the known detectors, in order to stabilize the sensibility, provide for a pre-radiation up to doses of 10 kGy with 20 MeV-electrons, so as to operate, during the radiotherapy, within the region in which the decay of sensibility is less pronounced.

After the pre-radiation, in fact, the dosimetric detector is used in clinical radiotherapeutic applications with radiation doses which are actually less intense but which, however, are cause for a slight reduction of sensibility, thereby calling for frequent and complex re-calibrations of the detector.

Another method used for lowering the dependence of the sensibility from the accumulated dose, is that of intentionally introducing an impurity in the crystalline silicon by adding platinum, for example, at a concentration far greater than that of the defects being created; in this way, even prior to the radiation, the extension of diffusion of the minority carriers L is reduced and its value stabilized according to the dose of accumulated radiation.

Also these methods are not without drawbacks.

In particular, by adding the platinum as an impurity, it is difficult to uniform it over the whole silicon layer, so that it is not actually possible to produce a matrix of sensible elements with the same characteristics throughout the surface of the crystalline silicon layer.

DISCLOSURE OF THE INVENTION

The object of the present invention is to overcome the above said drawbacks by providing a bidimensional dosimetric detector for radiotherapeutic applications which allows, with a suitable spatial resolution, to control the planned distribution of radiation dose upon the pre-treatment stage.

A second object of the present invention is to provide a bidimensional dosimetric detector which makes it possible to optimize the active thickness W of the detector, to make the dosimetric response stable with the accumulated dose, and to increase the spatial uniformity of the dosimetric response.

A further object of the dosimetric detector according to the present invention is to allow a great modularity of the disposition of the sensible elements and, thus, an increase of the spatial resolution, by using a monolithic base-matrix of crystalline silicon.

These and further objects that will appear more clearly by the detailed description that follows, are achieved according to the present invention by a bidimensional dosimetric detector for radiotherapeutic applications, having the structural and operational characteristics set forth in the appended independent claims. Further embodiments thereof being disclosed in the corresponding dependent claims.

The invention is illustrated hereinbelow in greater detail with reference to the accompanying drawings which show an exemplary and not limiting embodiment thereof. In the drawings.

With reference to the figures, the bidimensional dosimetric detector comprises a monolithic base-matrix made of crystalline silicon having preferably a square-shaped radiation surface and a thickness of the homoepitaxial layer of approximately 50 µm, one or more radiation-sensible elements 2 also of crystalline silicon and operatively associated with the radiation surface in order to produce a plurality of electrical signals in response to a radiation, and one or more electrical terminals 3 connected with the sensible elements 2 to feed the electrical signals, produced by said elements, to a processing unit 5 connected to the dosimeter via connectors 4.

Figure 4:
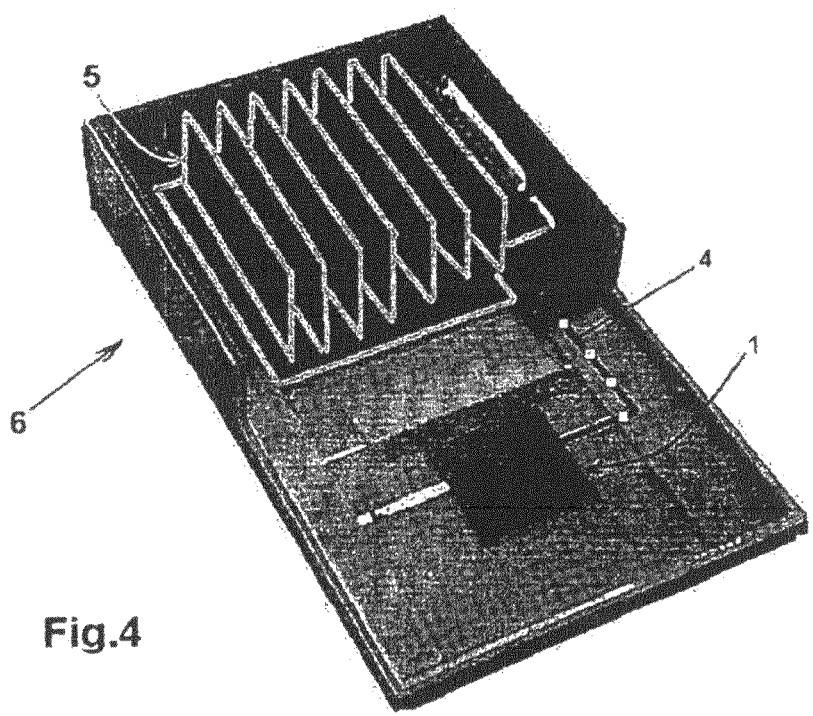
FIG. 4 shows a dosimeter according to the invention, complete with processing unit.

Referring now to FIG. 4, an exemplary preferred embodiment shown in this figure, the base-matrix 1 and unit 5 are received in a frame 6.

Figure 1:
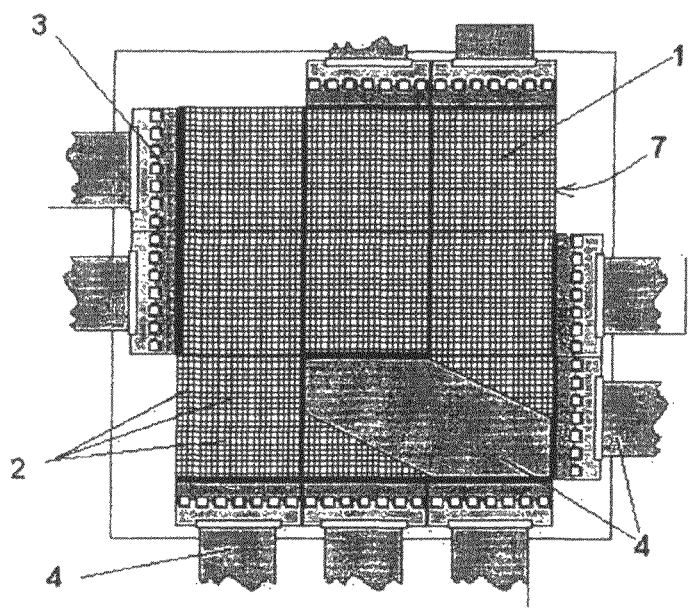
FIG. 1 shows a dosimetric detector, according to the present invention, obtained by composing nine monolithic base-matrixes.

Preferably, the frame 6 is able to receive a modular disposition of base-matrixes 1, for example a nine-element composition 7 as shown in FIG. 1.

In this case, the contacts 4 for the central element of composition 7 are disposed externally to make the connection with the unit 5 easier.

Advantageously, the sensible elements 2 are diodes encircled by a further arrangement $n^+$ indicated as guard ring.

Figure 5A:
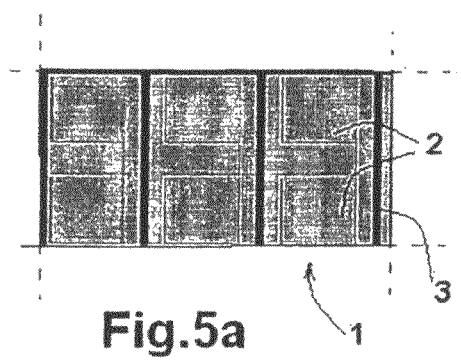
FIG. 5a shows a detail of the disposition of pixels within the dosimeter's matrix.
Figure 5B:
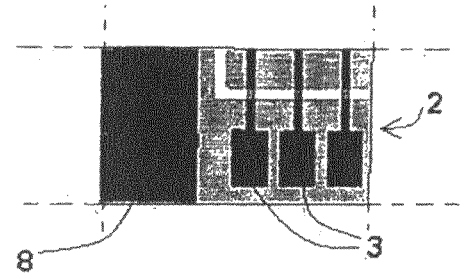
FIG. 5b shows a detail of the contacts and structure of a guard ring associated with the individual pixels of the dosimeter.

Represented respectively in FIGS. 5a and 5b, are a portion of base-matrix 1 with the disposition of the dosimeter's individual sensible elements 2 and a structure of contacts 3 and guard ring 8 associated therewith.

Preferably, the ring is disposed so as to encircle each square pixel at typically a distance of 20 µm from the perimeter of same pixel. The grid of guard rings so produced is grounded during the operation of the device, so as to confine the pixel's active volume and, thus, the response to the dose.

The invention proposes the use of crystalline silicon with extended diffusion length L (400-500 µm) and small thickness W (40-60 µm) of the silicon's active layer. Under these conditions, the active thickness of the detector is W and not L, as generally occurs in the known detectors.

It should be pointed out that this concept is valid as far as the accumulated doses are less than 10 kGy; this being a value that results, however, far higher than the total doses to which a silicon diode used in clinical radiotherapeutic applications is subjected.

To obtain a very extended L, use is made of crystalline-quality silicon.

The invention proposes using a layer of epitaxial silicon of p type, which is grown on a substrate of crystalline silicon, preferably, of Czochralski type.

This latter type of crystalline silicon exhibits a very low resistivity (0.01 Ωcm) and a diffusion length L in the order of a micron, which allows to consider as negligible the contribution of the charge generated on the detector's signal.

Moreover, using an epitaxial silicon of p type, allows growing, on the Czochralski substrate, a uniform layer of very small thickness that can be kept in the order of 50 µm with a tolerance of ±2 µm.

Figure 3:
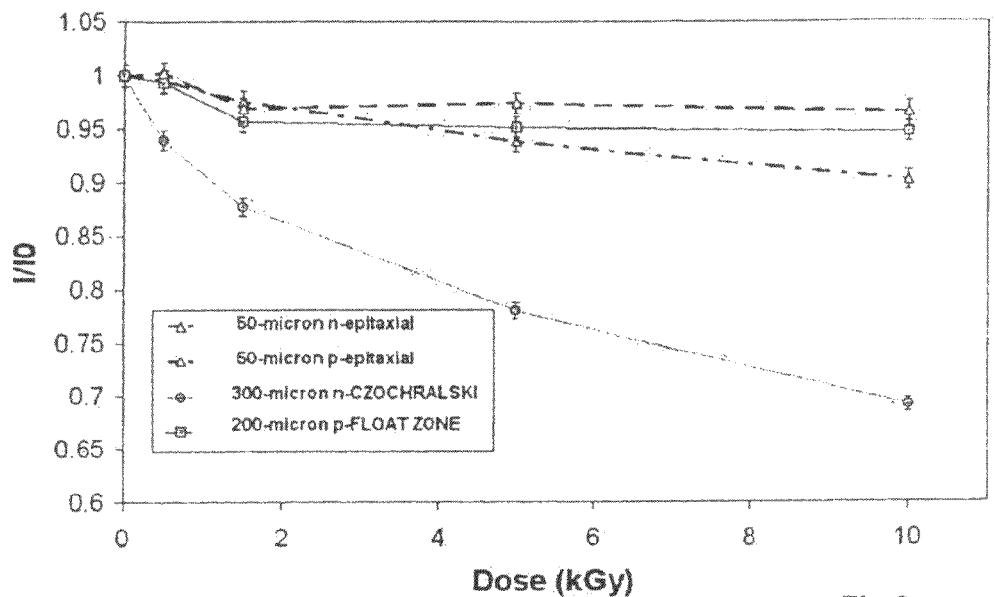
FIG. 3 is a graph of the electrical signal-versus-dose, as measured on various active thicknesses.

Shown in FIG. 3 is a graph of the electrical signal-versus-accumulated dose, normalized at zero-dose signal for different active thicknesses and for silicon materials grown by various techniques.

In the graph, it can be observed that the epitaxial diodes result the elements which resist more to the damage of the radiation dose, in particular, the epitaxial material of p type exhibits the smallest reduction of sensibility upon an increase of the radiation dose.

The invention achieves major advantages.

First of all, a high stability of the signal occurs for doses lower than 10 kGy of 20 MeV-electrons, wherein the diffusion length L is about 60 µm.

Moreover, in comparison with the platinum-doped diode, the active thickness W of the detector according to the invention is far greater, thereby allowing a higher sensibility of the device and the possibility of using the latter with lower dose-rates.

A further advantage lies in the fact that the higher response uniformity of the monolithic base-matrix 1 makes it possible to create diode matrixes 2 starting from individual wafers which may be also of extended area.

An equally important advantage is given by the use of epitaxial silicon of p type which results less subject to damages from radiation doses and, for this reason, more stable on the whole in the subsequent utilizations.

Figure 2:
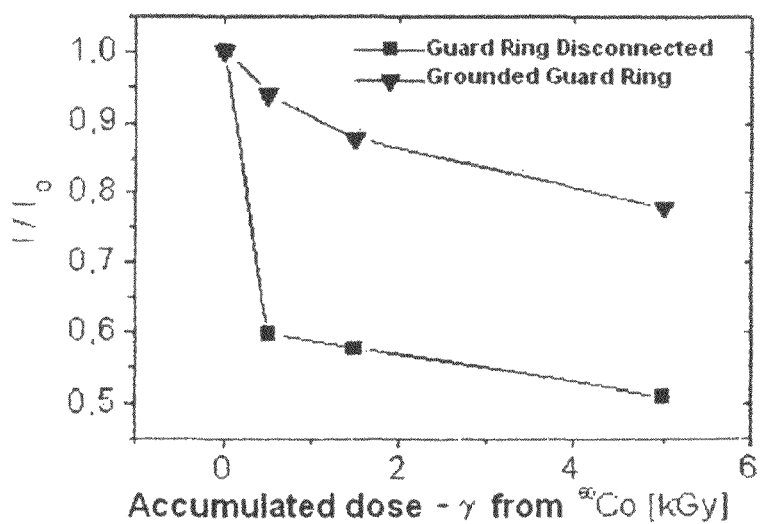
FIG. 2 is a graph showing the efficacy of a guard ring over the stabilization of the signal.

Advantageously, as shown in FIG. 2, by using the guard ring, the reduction of the electrical signal, upon an increase of the absorbed dose, is much less high.

This aspect has been assessed on a 300 µm-thick silicon diode with guard-ring structure at 20 µm from the front contact, by irradiating the same diode at a dose of 5 kGy with $^{60}CO$ with four successive radiations. After each radiation, the diode sensibility was measured with a radiotherapeutic beam of $^{60}CO$ in the two configurations: connected guard ring and disconnected guard ring.

As previously pointed out, the invention has been described with reference to a preferred embodiment based on the modular composition of a monolithic base-matrix of active elements (pixels), each consisting of a junction surrounded by a guard ring, wherein the pixels lie on a single slice of material consisting of an epitaxial layer grown on crystalline silicon.

In this embodiment, the pixels are provided with electrical terminals all disposed on a single side of the matrix for a real-time gathering, by a suitable acquisition and processing unit, of the electrical signal in response to the radiation. Moreover, the guard rings are also provided with electrical terminals, and are grounded for the lateral boundary-violation of the active region.

In particular, a composition of up to nine base-matrixes has proved to be suited for determining the dose's bidimensional distribution on radiation surfaces of up to 28×28 $cm^2$ from the pitch of the base-matrix. However, it is understood that equivalent modifications could be made without departing from the scope of protection granted to the present industrial patent.

The invention claimed is:

1. A bi-dimensional dosimetric detector, comprising: a monolithic base-matrix made of homoepitaxial silicon having a first type doping and a surface for exposition to radiation, a plurality of radiation-sensitive junction diodes having a second type doping for producing a plurality of electrical signals in response to the radiation, electrical terminals connected to said diodes for feeding said produced electrical signals to an acquisition and processing unit, wherein a perimeter of one or more of said radiation-sensitive junction diodes is defined by a guard ring having a same doping type of said radiation-sensitive junction diodes, said guard ring and said radiation-sensitive junction diodes being separated by a region having a same doping type of said homoepitaxial silicon.

2. A dosimetric detector according to claim 1, wherein said radiation surface is of square shape.

3. A dosimetric detector according to claim 1, wherein said monolithic base-matrix is included in a modular composition of more base-matrixes.

4. A dosimetric detector according to claim 1, wherein said electrical terminals of each base-matrix, all lead to only one side to facilitate the connection thereof to the acquisition and processing unit.

5. A dosimetric detector according to claim 1, wherein said monolithic base-matrix comprises a p-type epitaxial silicon layer which is grown on a substrate of Czochralski crystalline silicon.

6. A dosimetric detector according to claim 5, wherein said p-type epitaxial silicon layer has a thickness in a range of 48 to 52 µm.

7. A dosimetric detector according to claim 1, wherein said perimeter of said diodes consists of a grid-shaped guard ring to confine both the active volume and the response of each single diode.

8. A dosimetric detector according to claim 7, wherein said guard ring comprises a grounded connection.

9. A dosimetric detector according to claim 1, wherein said diodes have a thickness W less than or equal to L, L being the diffusion length of the minority carriers in the epitaxial layer.

10. A dosimetric detector according to claim 1, wherein the first type doping type is p-type doping and the second type doping is n-type doping.

11. A dosimetric detector according to claim 1, wherein the first type doping type is n-type doping and the second type doping is p-type doping.

12. A dosimetric detector according to claim 1, wherein said region separating the guard ring and said radiation-sensible junction diodes have different concentrations of the first type doping type.

13. A dosimetric detector according to claim 1, wherein said guard ring and said radiation-sensible junction diodes have different concentrations of the second type doping.

14. A method for dosimetric simulations in radiotherapeutic applications using a bidimensional detector, comprising the steps of: (a) providing a monolithic base-matrix made of homoepitaxial silicon having a first type doping and a surface for exposition to radiation, one or more junction diodes having a second type doping for producing one or more electrical signals in response to exposition to the radiation wherein a perimeter of one or more said radiation-sensible junction diodes is defined by a guard ring having a same doping type of said radiation-sensible junction diodes, said guard ring and said radiation-sensible junction diodes being separated by a region having a same doping of said homoepitaxial silicon, electrical terminals connected to said diodes for feeding said electrical signals to a processing unit; (b) exposing said monolithic base-matrix to radiation; and (c) collecting the resulting signals at said electrical terminals.

15. A method according to claim 14, wherein said perimeter consists of a grid-shaped guard ring to confine both the active volume and the response of each single diode.

* * * * *